United States Patent [19]

Inman et al.

[11] 4,038,241
[45] July 26, 1977

[54] POLYMER COMPOSITIONS CONTAINING A BISAZOMETHINE PIGMENT

[75] Inventors: Eric Richard Inman, Bridge of Weir; James McGeachie McCrae, Stewarton; Christopher Midcalf, Kilbarchan; Alison Turner, Houston, all of Scotland

[73] Assignee: Ciba-Geigy Corporation, Ardsley, N.Y.

[21] Appl. No.: 526,283

[22] Filed: Nov. 22, 1974

Related U.S. Application Data

[62] Division of Ser. No. 333,598, Feb. 20, 1973, Pat. No. 3,864,371.

[30] Foreign Application Priority Data

Feb. 24, 1972 United Kingdom .................. 8517/72

[51] Int. Cl.$^2$ ........................ C08K 5/35; C08L 23/02; C08L 25/06; C08L 75/04
[52] U.S. Cl. .................................. 260/39 P; 106/20; 106/241; 260/37 N; 260/37 NP; 260/42.21
[58] Field of Search ...................... 106/20, 22, 23, 31, 106/32, 288 Q, 241; 260/429 C, 439 R, 37 NP, 39 P, 37 N, 42.21, 42.46

[56] References Cited

U.S. PATENT DOCUMENTS

| | | | |
|---|---|---|---|
| 2,993,065 | 7/1961 | Kumins et al. | 260/439 R |
| 3,440,254 | 4/1969 | Lenoir et al. | 260/439 R |
| 3,441,578 | 4/1969 | Dimroth | 260/439 R |
| 3,687,991 | 8/1972 | Gaeng | 260/429 C |

*Primary Examiner*—Allan Lieberman
*Attorney, Agent, or Firm*—Vincent J. Cavalieri

[57] ABSTRACT

Polymer compositions containing as a pigment a compound having the formula:

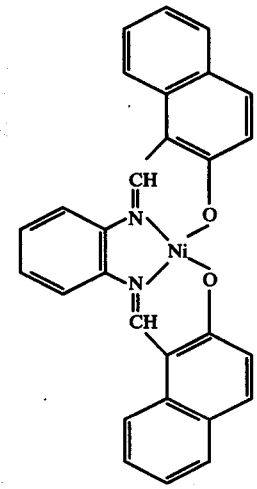

in the pigmentary form in which it has an orange-red color and has an X chromaticity co-ordinate of from 0.59 to 0.63 and a Y chromaticity of from 0.33 to 0.36, each as hereinbefore defined.

9 Claims, No Drawings

POLYMER COMPOSITIONS CONTAINING A BISAZOMETHINE PIGMENT

This is a divisional of application Ser. No. 333,598, filed on Feb. 20, 1973 now U.S. Pat. No. 3,864,371, which issued Feb. 4, 1975.

The present invention is concerned with a new pigmentary form of the nickel complex of the bisazomethine from o-phenylene diamine and 2-hydroxynaphth-1-aldehyde.

This nickel complex which has the formula I

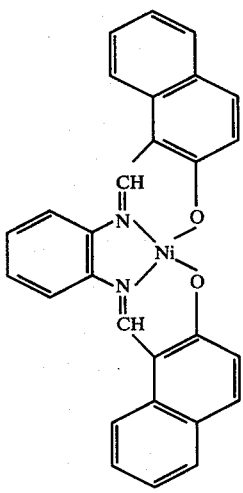

is a chemical compound known per se. It was first prepared by Mukherjee & Ray (page 606 of the Journal of the Indian Chemical Society 1955, Vol. 32), by a conventional metallisation of the ligand itself first prepared by Pfeiffer et al. and described in the Journal Praktische Chemie 1937, Vol. 149 at page 247.

Its direct preparation from β-naphthol and o-phenylenediamine and its use as a golden brown pigment were described in U.S. Pat. No. 2,993,065 in 1961. The product, prepared as described in this patent is impure and even after purification by the recommended solvent extraction retains its characteristic golden brown shade which has not found favour in commerce.

We have now discovered that this compound exists in an attractive orange-red form which retains the fastness to light and weathering of the golden brown pigment and, in addition, possesses increased colouring power. Such a pigment is particularly valuable; as lightfast coatings of this shade, for example, for automotive lacquers, have hitherto had to be formulated by using either expensive dibromoanthanthrone pigments or lead pigments now considered undesirable on health grounds.

The exact physical nature of this pigmentary form is not known. Surprisingly, it does not differ significantly in analysis or in its X-ray diffraction pattern from the known form, but it can be clearly differentiated and defined by reference to the system of the Commission Internationale d'Eclarage (C.I.E.) as set out in 1931 using for convenience a 3% unreduced pigmentation in an alkyl melamine stoving lacquer illuminated by north facing daylight or its equivalent (Illuminance C of the C.I.E.). For this measurement, the pigment is incorporated into the lacquer by ball milling and applied to white card using either an applicator or by spraying in a conventional manner. The chromaticity coordinates are measured using a recording spectrophotometer fitted with a tristimulus integrator.

The product of this invention is characterised by having an orange-red colour possessing, under the conditions defined by the C.I.E. system and set out above, and $x$ chromaticity coordinate of from 0.59 to 0.63 and a $y$ chromaticity coordinate of from 0.33 to 0.36. It is distinguised from the known golden brown form whose chromaticity coordinates are $x=0.55-0.58$ and $y=0.365-0.39$.

Two methods of preparation are particularly advantageous for the direct preparation of this new orange red pigmentary form of the metal complex of Formula I.

In the first method, the 1:1 nickel complex of 2-hydroxy-1-naphthaldehyde is initially prepared as a very finely divided suspension in water by reacting 2-hydroxynaphth-1-aldehyde and a water soluble nickel salt at pH 7-9 preferably in the presence of a small amount, for example, 0.1%, of a nonionic surfactant using very efficient agitation. The complex is then further reacted with the appropriate amount of o-phenylene diamine under the same conditions except that the temperature is gradually raised to 90° – 100° C. and held there until reaction is complete.

In the second method, the azomethine of formula II:

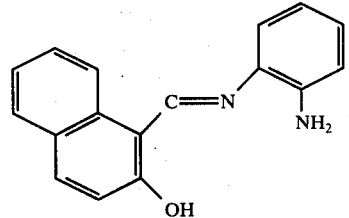

may be reacted under the same conditions, first with a water soluble nickel salt and afterwards with a further molecule of 2-hydroxynaphth-1-aldehyde.

In both methods the pH is controlled by the use of a buffer salt for which purpose sodium acetate is particularly suited.

The compound of formula I may be employed as a pigment directly after its production according to a process of this invention, that is after it has been filtered off from its reaction mixture and dried. Alternatively, it may be further processed using a wet or dry conditioning technique such as grinding, either alone or in the presence of a water-soluble salt or other medium which can subsequently be removed, for instance by washing.

Because of its economical and easy mode of production, combined with its excellent pigmentary properties, the compound of the invention is valuable for use as a pigment in a wide variety of organic media, for instance natural and synthetic polymeric materials such as rubber, polyolefines, polystyrene, polyurethanes and resinous materials. Of particular interest are surface coating media, such as paints, inks and lacquers.

Accordingly, the present invention also provides a composition comprising an organic material containing, as pigment, a compound of the invention as hereinbefore defined.

Some Examples will now be given. Parts and percentages shown are by weight unless otherwise stated.

EXAMPLE 1

17.2 Parts of 2-hydroxy-1-naphthaldehyde were suspended in a solution consisting of 300 parts water, 16.0 parts sodium acetate trihydrate and 0.1 part of a condensate of nonylphenol and ethylene oxide which is a non-ionic surfactant sold under the trade mark Lissapol NX, and the suspension was stirred at room temperature with high speed shear agitation for 15 minutes. To the cream coloured suspension resulting, there was added a solution of 16.0 parts of nickel nitrate hexahydrate dissolved in 50 parts of water, and the resultant lime green suspension was stirred as before, for 30 minutes. After the addition of 5.4 parts of o-phenylene diamine, the mixture was stirred for 45 minutes to give a buff-coloured suspension which, on heating to 95° C. over the course of 5 minutes, became red brown in colour whilst the pH changed from 7–8 to 4. A solution of 16.0 parts sodium acetate trihydrate in 50 parts of water was then added and the temperature was maintained at 97°–99° C. for 1 hour whereupon a deep red suspension was obtained. This suspension was filtered hot, the filter-cake washed with 1,500 parts of hot water and then dried, giving 23.0 parts (97.5% of theory) of an orange red powder which did not melt below 360° C. Ni = 13.8% (theory 12.4%). Chromaticity co-ordinates: $X = 0.62, y = 0.34$.

EXAMPLE 2

13.1 Parts of an aqueous paste of 2-amino-N'-(2-hydroxy-naphthylidene) aniline (II) (100% actual pigment) were suspended in 1,000 parts water containing 0.1 part of Lissapol NX and dispersed using high speed shear agitation for 5 minutes. A solution of 7.7 parts of sodium acetate trihydrate in 50 parts water was added and the whole stirred for 5 minutes; next a solution of 14.54 parts nickel nitrate hexahydrate in 100 parts water was added and the mixture stirred for 5 minutes, and finally a solution of 7.7 parts sodium acetate trihydrate in 50 parts water was added and the mixture stirred for a further 10 minutes.

8.6 Parts of 2-hydroxy-1-naphthaldehyde were added over 1½ minutes and the resultant suspension stirred at room temperature for 7 minutes before being heated to 99° C. over the course of 13 minutes to give a red-brown suspension of pH 5. The pH was adjusted to 7 by adding a solution of 7.7 parts sodium acetate trihydrate in 50 parts water and the suspension held at 97°–99° C. for 1 hour, after which time no reaction of the liquors with dimethylglyoxime was obtained. A deep orange red solid was filtered off, the filter-cake washed with 2,000 parts hot water and dried, giving 22.3 parts (95% of theory) of orange red powder which did not melt below 360° C. Chromaticity co-ordinates: $x = 0.62, y = 0.34$

EXAMPLE 3

60 Parts of the product of Example 1 were ball milled with 138 parts of a solution of an unmodified butylated melamine/formaldehyde resin in n-butanol sold under the trade mark "Epok U9193" and 452 parts of xylene. 350 parts of a solution of a hydroxy acrylic resin in a 1:1 mixture of xylene and n-butanol sold under the trade mark "Epok D2103" were then added gradually and ball milling continued. The resulting paint had a pigment to binder ratio of 1:5. This was adjusted to 1:10 by the addition of more resin solution and the paint was thinned to the required viscosity for spraying. Aluminium panels were sprayed with this lacquer and then stoved at 120° C. for 30 minutes. The resulting orange red paint films had excellent fastness to light, heat and acids, and were only slightly altered on exposure to a Xenon arc weathering lamp for 1,000 hours.

What we claim is:

1. A composition comprising a natural or synthetic polymer containing, as pigment, a compound of the formula

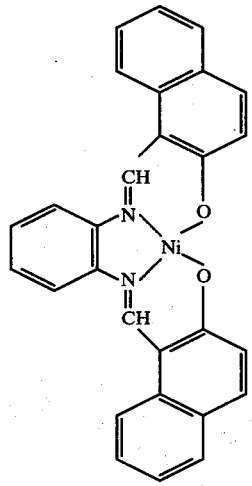

in the pigmentary form in which it has an orange-red color and has an X chromaticity co-ordinate of from 0.59 to 0.63 and a Y chromaticity of from 0.33 to 0.36.

2. A composition of claim 1 wherein the polymer is a resinous material.

3. A composition of claim 1 wherein the polymer is rubber.

4. A composition of claim 1 wherein the polymer is a polyolefin.

5. A composition of claim 1 wherein the polymer is polystyrene.

6. A composition of claim 1 wherein the polymer is polyurethane.

7. A composition of claim 1 wherein the polymer is a butylated melamine/formaldehyde resin and a hydroxy acrylic resin.

8. A composition as claimed in claim 1, wherein the organic material is a surface coating medium.

9. A composition as claimed in claim 8, wherein the surface coating medium is a paint, lacquer or ink.

* * * * *